US010426647B2

(12) United States Patent
Romo et al.

(10) Patent No.: US 10,426,647 B2
(45) Date of Patent: Oct. 1, 2019

(54) ORTHOPEDIC DEVICE

(71) Applicant: Ossur Iceland ehf, Reykjavik (IS)

(72) Inventors: Harry Duane Romo, Aliso Viejo, CA (US); Jonathan Walborn, Mission Viejo, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 813 days.

(21) Appl. No.: 15/011,872

(22) Filed: Feb. 1, 2016

(65) Prior Publication Data

US 2016/0220409 A1 Aug. 4, 2016

Related U.S. Application Data

(60) Provisional application No. 62/252,696, filed on Nov. 9, 2015, provisional application No. 62/147,459, filed on Apr. 14, 2015, provisional application No. 62/110,845, filed on Feb. 2, 2015.

(51) Int. Cl.
*A61F 5/01* (2006.01)

(52) U.S. Cl.
CPC ............ *A61F 5/0127* (2013.01); *A61F 5/013* (2013.01); *A61F 5/0113* (2013.01)

(58) Field of Classification Search
CPC ...... A61F 5/0111; A61F 5/0113; A61F 5/0127
USPC ...................................... 602/27, 28
See application file for complete search history.

(56) References Cited

U.S. PATENT DOCUMENTS

| 4,556,054 A | 12/1985 | Paulseth |
| 4,646,726 A | 3/1987 | Westin et al. |
| 5,069,202 A * | 12/1991 | Prock .................... A61F 5/0127 602/27 |
| 5,167,612 A | 12/1992 | Bonutti |
| 5,376,068 A | 12/1994 | Grifka |
| 5,902,259 A | 5/1999 | Wilkerson |
| 8,202,239 B2 | 6/2012 | Wilkerson |
| 8,277,401 B2 | 10/2012 | Hammerslag et al. |
| 8,657,773 B2 * | 2/2014 | Ostergard ............. A61F 5/0111 36/88 |
| 2002/0169403 A1 | 11/2002 | Voskuilen |
| 2009/0299245 A1 | 12/2009 | Wilkerson |

(Continued)

OTHER PUBLICATIONS

International Search Report from PCT Application No. PCT/US2016/015908, dated May 31, 2016.

*Primary Examiner* — Keri J Nelson
(74) *Attorney, Agent, or Firm* — Workman Nydegger

(57) ABSTRACT

An orthopedic device includes a footplate defining opposing first and second sides and an upright support having a distal portion connected to the first side of the footplate. A motion control system controls movement of the second side of the footplate by anchoring at least one tensioning element to the second side of the footplate at a first guide while guiding the at least one tensioning element above the footplate through a second guide on an upper anchor element. The at least one tensioning element is arranged to allow movement of the second side of the footplate in a direction away from the upper anchor element until the at least one tensioning element becomes taut and to slide through the first and second guides when a proximal portion of the upright support moves toward and away from an anterior end of the footplate.

14 Claims, 5 Drawing Sheets

(56) References Cited

U.S. PATENT DOCUMENTS

2012/0304356 A1 12/2012 Brewer
2014/0276318 A1 9/2014 Faux

* cited by examiner

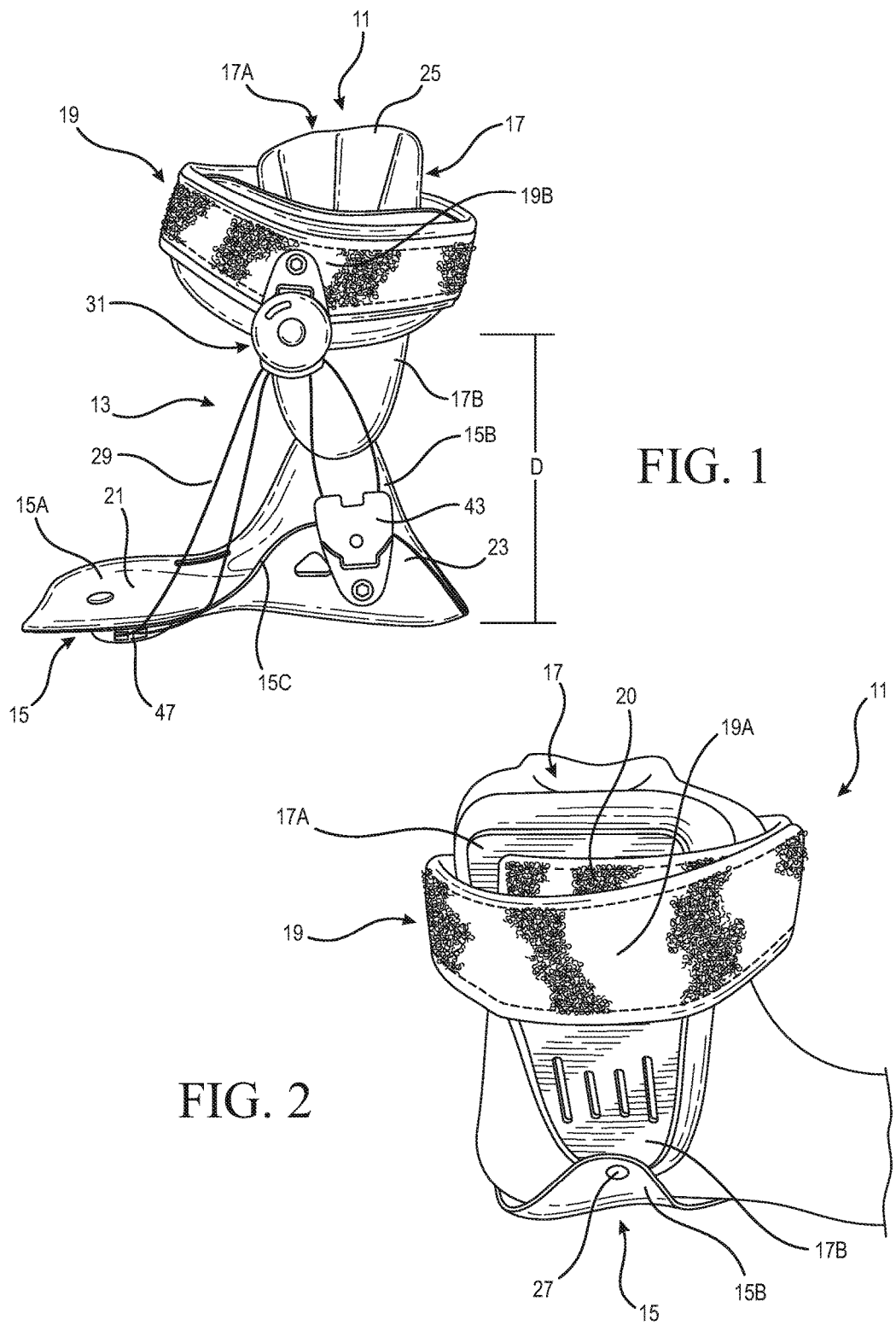

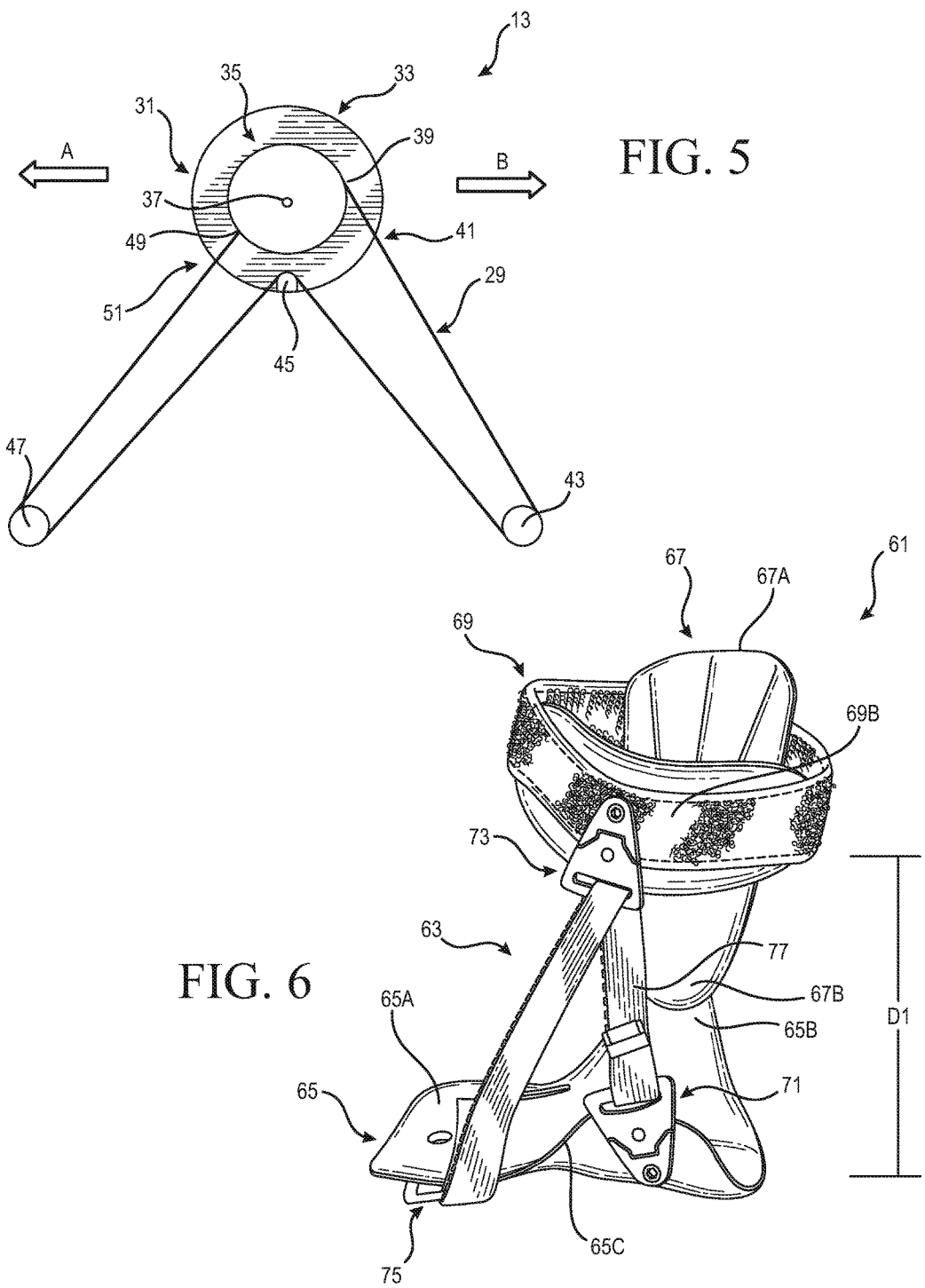

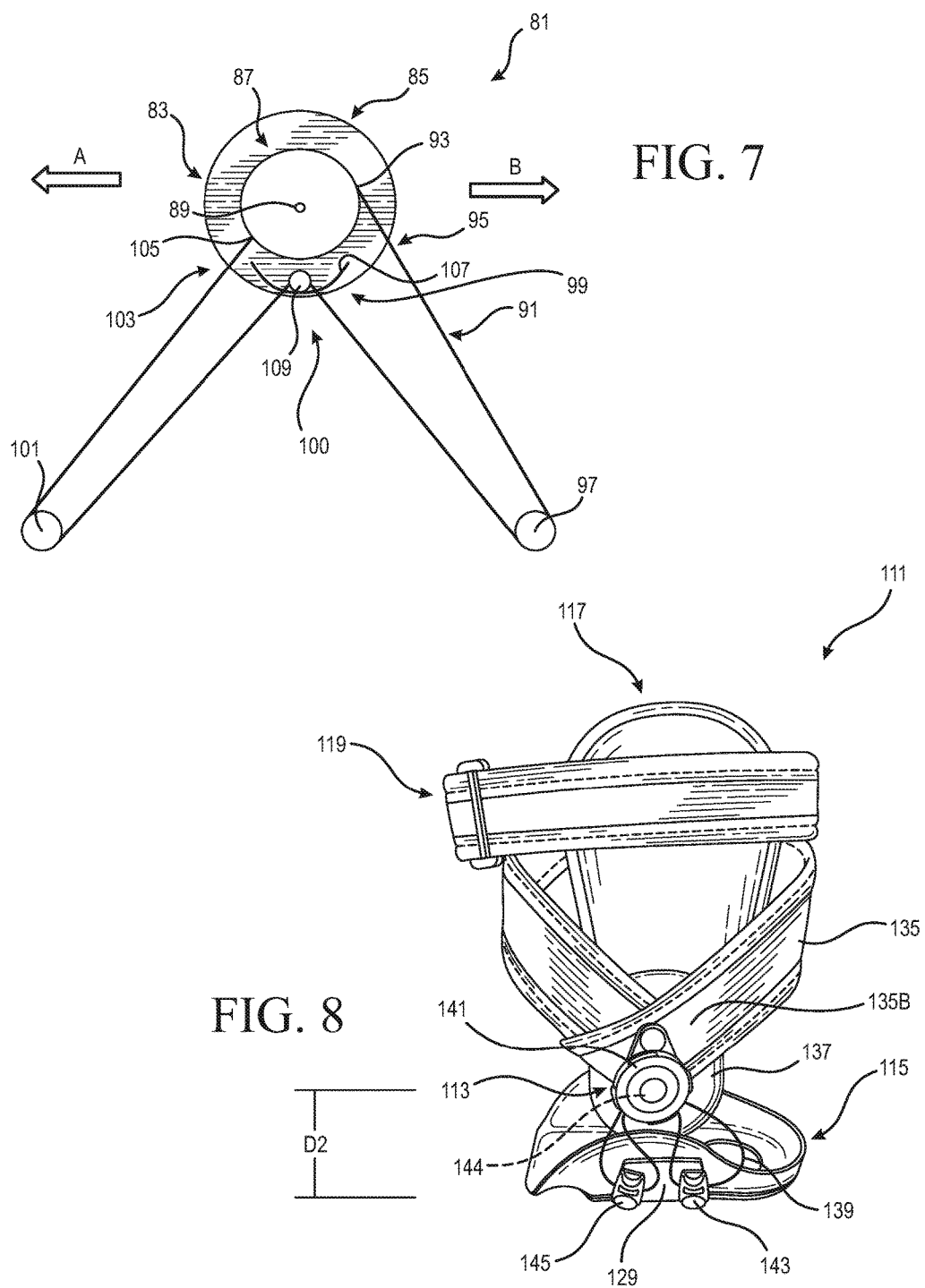

ORTHOPEDIC DEVICE

TECHNICAL FIELD

The disclosure relates to an orthopedic device for controlling motion of the foot and/or other anatomical areas.

BACKGROUND

Ankle braces and supports are designed to provide compression and support to mild to moderate ankle strains and sprains. These braces typically accommodate an ankle so that the wearer can continue with daily activities despite injury. Such braces may also be arranged to offer additional support in prevention or in post injury situations whether the brace is adapted for daily walking or participating in physical activities.

Many of these ankle braces provide only limited prevention of inversion (the foot rolling inward) and eversion (the foot rolling outward), which is the most commonly occurring type of ankle injury. Those designed to provide better inversion/eversion control often limit plantar flexion and dorsiflexion, which can make such braces uncomfortable to use and impractical for use during athletic or other events including higher activity levels. Further, typical ankle braces are not readily customizable and cannot be easily adjusted to accommodate wearers' preferences and/or activity levels.

There exists a need for improved orthopedic devices for controlling inversion/eversion of the foot that allow for normal plantar flexion/dorsiflexion and that are easily adjustable to accommodate individual preferences and/or activity levels.

SUMMARY

Embodiments of the orthopedic device advantageously provide both support and freedom of motion to a wearer's foot and/or other anatomical areas. According to an embodiment, the orthopedic device can include a footplate defining an anterior end, a first side, and a second side opposite the first side. The second side can define a first guide. An upright support can include a distal portion connected to the first side of the footplate and a proximal portion arranged to move toward and away from the anterior end of the footplate.

A motion control system controls movement of the second side of the footplate by anchoring at least one tensioning element to the second side of the footplate at a first guide while guiding the at least one tensioning element above the footplate through a second guide on an upper anchor element. When the orthopedic device is worn and the wearer's foot undergoes coronal plane motion (e.g., inversion or eversion), the second side of the footplate can tend to move with the foot away from the upper anchor element. If present, slack in the at least one tensioning element extending between the upper anchor element and the footplate can allow for some movement of the second side of the footplate away from the upper anchor element but such movement is limited as the at least one tensioning element becomes taut or reaches a hard-stop, thereby restricting and/or controlling coronal plane motion of the foot.

The at least one tensioning element is arranged to pass, slip, or slide through the first and second guides as the upper anchor element and/or the proximal portion of the upright support move toward and away from the anterior end of the footplate during gait. This advantageously allows the orthopedic device to restrict or control coronal plane motion of the foot while also accommodating dorsiflexion and/or plantar flexion of the foot in the sagittal plane, providing a more comfortable and natural fit.

According to a variation, movement of the second side of the footplate away from the upper anchor element can be further controlled by varying the length of the at least one tensioning element extending between the upper anchor element and the footplate. This allows a wearer to quickly and easily control the amount of tension in the at least one tensioning element and coronal plane motion permitted by the orthopedic device, providing the wearer the ability to customize the orthopedic device. The wearer can also vary the length of the at least one tensioning element to adjust the level of restriction to the physical needs of the wearer.

According to a variation, the motion control system is arranged to dynamically link sagittal plane motion to coronal plane motion of the foot and/or vice versa. This is advantageous because a common mechanism of injury in ankle sprains is a combination of plantar flexion and inversion. By linking plantar flexion and inversion/eversion movement of the user's foot, the orthopedic device and motion control system can selectively control such movements and/or provide additional stability, facilitating range-of-motion rehabilitation, progressive muscle-strengthening exercises, proprioceptive training, and/or activity-specific training. It can also be used prophylactically for higher-risk patients or during high-risk activities such as volleyball or basketball.

BRIEF DESCRIPTION OF THE DRAWINGS

These and other features, aspects, and advantages of the present disclosure will become better understood regarding the following description, appended claims, and accompanying drawings.

FIG. 1 is a side isometric view of an ankle brace according to an embodiment.

FIG. 2 is another side isometric view of the ankle brace shown in FIG. 1.

FIG. 5 is a schematic view of the motion control system according to an embodiment.

FIG. 6 is a side isometric view of an ankle brace according to another embodiment.

FIG. 7 is a schematic view of a motion control system according to another embodiment.

FIG. 8 is a side isometric view of an ankle brace according to another embodiment.

DETAILED DESCRIPTION OF VARIOUS EMBODIMENTS

Figure 3:
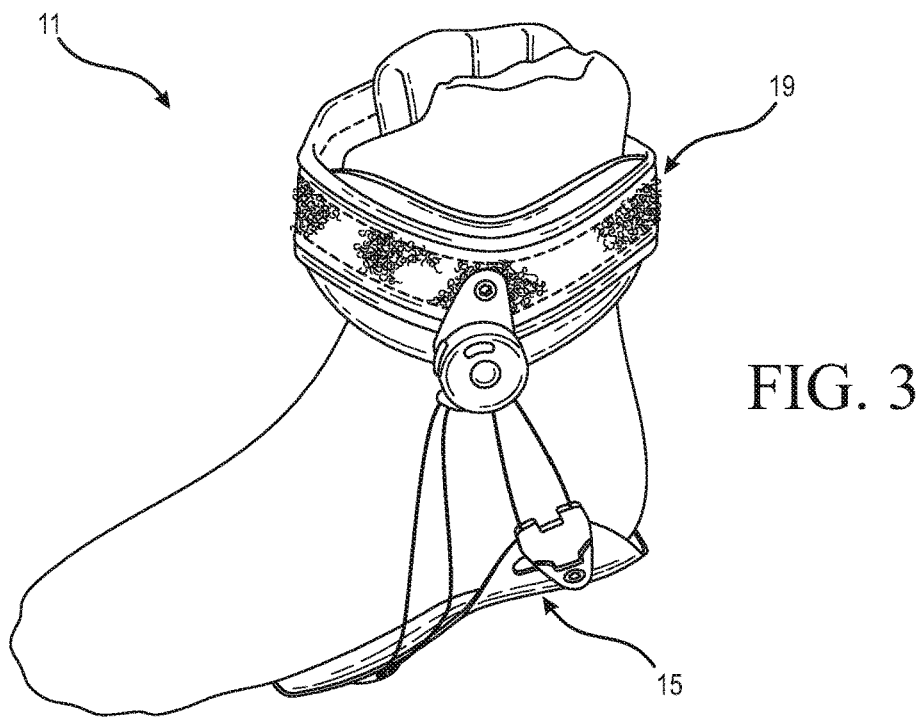
FIG. 3 is another side isometric view of the ankle brace shown in FIG. 1.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and described below. It should be understood, however, there is no intention to limit the disclosure to the embodiments disclosed, but on the contrary, that the intention covers all modifications, alternative constructions, combinations, and equivalents falling with the spirit and scope of the disclosure.

For further ease of understanding the embodiments of an orthopedic device as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and that in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members or shells that provide support and are free-standing; however, such support members or shells may have some degree of flexibility or resiliency.

The exemplary embodiments of the orthopedic device with an integrated motion control system can include configurations of ankle braces or orthopedic devices in other anatomical areas such as the hip or the shoulder.

FIGS. 1-5 show an embodiment of the orthopedic device comprising an ankle brace 11 and an integrated motion control system 13 arranged to control coronal plane motion of the foot (e.g. limiting inversion/eversion), while allowing plantar flexion and dorsiflexion of the foot in the sagittal plane, providing a more comfortable fit and accommodating a more natural motion of the foot and ankle. The motion control system 13 also beneficially permits custom management of the overall brace tightness or control based on a wearers' preference and/or activity level. As seen, the ankle brace 11 can include a footplate 15, an upright or medial support 17, and a strap member or cuff 19.

The footplate 15 is adapted to be positioned beneath the foot of a wearer. The footplate 15 can have a semi-rigid configuration and extends between an anterior end 15A and a posterior end section. The footplate 15 defines an upper surface 21 contoured to generally correspond to the plantar surface of the foot and one or more side edges 23 that extend around and up the medial and lateral sides of the ankle.

The medial support 17 is connected to a first or medial side 15B of the footplate 15. The medial support 17 defines a distal portion 17B connected to the medial side 15B of the footplate 15 and a proximal portion 17A arranged to move toward and away from the anterior end 15A of the footplate 15. The medial support 17 is adapted to extend along the medial side of the ankle and can have a semi-rigid configuration.

A soft good support 25 provided on an inner surface of the medial support 17 that is arranged to engage the medial side of the ankle in order to provide comfort and a proper fit of the ankle brace 11.

As best seen in FIG. 2, the distal portion 17B of the medial support 17 can be pivotally connected to the medial side 15B of the footplate 15 at a pivot axis or pivot point 27. This allows the proximal portion 17A of the medial support 17 to pivotally move about the pivot point 27 relative to the anterior end 15A of the footplate 15 such that the ankle brace 11 can accommodate plantar flexion and dorsiflexion. The pivot point 27 can be generally in line with the pivot of the ankle joint.

While the distal portion 17B is shown being pivotally connected to the medial side 15B of the footplate 15, in other embodiments, the distal portion 17B can be connected to the medial side 15B of the footplate 15 and the medial support 17 can bend, hinge, and/or flex to allow the proximal portion 17A to move toward and away from the anterior end 15A of the footplate 15.

The footplate 15 and the medial support 17 can provide the main structure of the brace 11, both supporting the foot and providing attachment points for the motion control system 13 described below.

The cuff 19 is attached to and extends from the proximal portion 17A of the medial support 17. The cuff 19 includes a medial side 19A attached to the medial support 17 and a lateral side 19B located a distance above the footplate 15. The cuff 19 can have a flexible or semi-flexible configuration, allowing at least the lateral side 19B of the cuff 19 to move toward and/or away from the upper surface 21 of the footplate 15.

The cuff 19 is arranged to extend around the calf, near or just proximal of the malleoli as seen in FIG. 3. The cuff 19 can include one or more ends removably attached to the medial support 17. The cuff 19 allows the brace 11 to be easily donned and doffed and can be selectively fastened securely around the calf so that in use the brace 11 does not slide up and down on the ankle.

It will be appreciated that the cuff 19 can be attached to the proximal portion 17A of the medial support 17 in any suitable manner but is shown being attached via a hook and loop type closure system 20. The medial support 17 extending between the cuff 19 and the medial side of the footplate 15 prevents movement of the medial side of the footplate 15 away from the cuff 19, restricting eversion of the foot when the ankle brace 11 is worn.

The lateral side 19B of the cuff 19 further provides an attachment point for the motion control system 13. Referring again to FIG. 1, the motion control system 13 includes a tensioning element 29, such as a cable, that is secured to an upper anchor element 31 arranged to operatively anchor the tensioning element 29 above the footplate 15. The upper anchor element 31 can comprise any suitable anchoring element but is shown being a tensioning control mechanism 31 arranged to anchor and adjust the length of the cable 29 extending between the footplate 15 and the cuff 19. The cable 29 can be a cable, a lace, wire or any other suitable member and may refer to a relatively long and relatively thin shaped metals or polymers, which may be single strand or multi-strand, and which may include friction reducing coatings thereon.

The tensioning control mechanism 31 can be a dial-tensioning control mechanism 31 arranged for incremental and preselected adjustment in the tension of the tensioning element 29. The dial-tensioning control mechanism 31 may be rotated in a first direction to decrease the length of the cable 29 and thereby increase the tension in the cable 29.

To increase the length of the cable 29 and thereby decrease the tension in the cable 29, the dial-tensioning control mechanism 31 may be rotated in a second direction. The tensioning control mechanism 31 is not limited to the example provided above but can include any system that permits adjusting tension in the tensioning element. The tensioning control mechanism 31 also allows the tensioning element 29 to be fixed at a desired length.

The dial-tensioning control mechanism 31 can be centrally secured to the lateral outer surface of the cuff 19, with the cable 29 extending from both the anterior and posterior sides of the dial-tensioning control mechanism 31 to the footplate 15. It should be noted that the ends of the cable 29 are retained within the dial-tensioning control mechanism 31 and the portion of the cable 29 outside the dial-tensioning control mechanism 31 extends continuously between the footplate 15 and the dial-tensioning control mechanism 31 without interruption.

Figure 4:
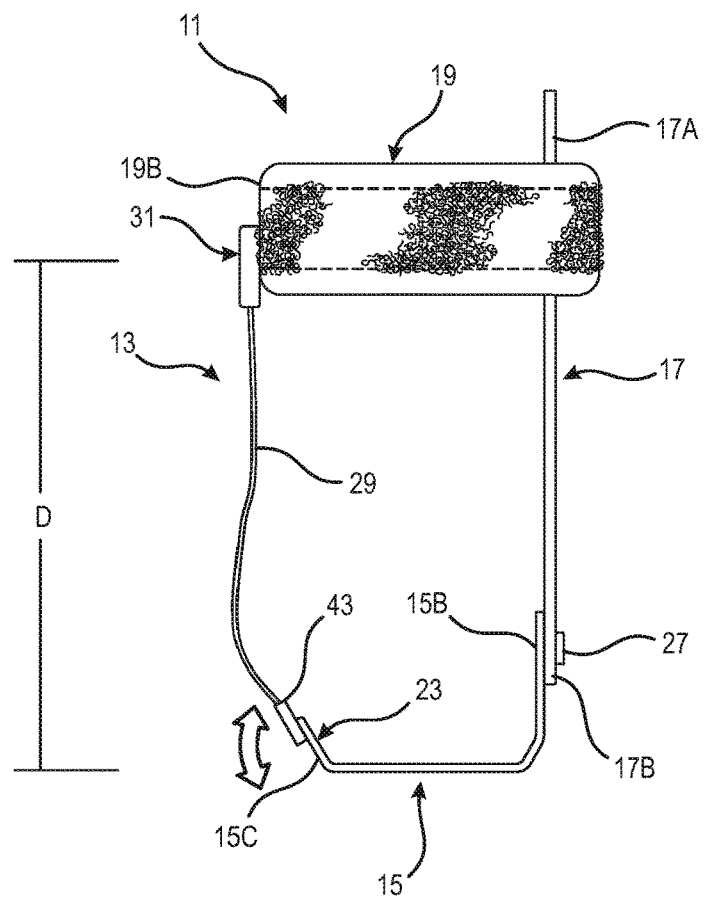
FIG. 4 is a schematic back view of the ankle brace shown in FIG. 1.

Referring to FIG. 4, the dial-tensioning control mechanism 31 is spaced apart from the lateral side 15C of the footplate 15 by a distance D (shown in FIGS. 1 and 4). As the dial-tensioning control mechanism 31 is regulated to decrease the length of the cable 29, the dial-tensioning mechanism 31 on the cuff 19 and the lateral side 15C of the footplate 15 can be urged or moved toward one another to decrease the distance D. As the dial-tensioning control mechanism 31 is regulated to increase the length of the cable 29, slack in the cable 29 can permit the dial-tensioning control mechanism 31 on the cuff 19 and the lateral side 15C of the footplate 15 to move apart and increase the distance D before the cable 29 reaches a hard stop or becomes taut.

As seen in FIG. 5, the dial-tensioning control mechanism 31 can include a base 33 and a reel assembly 35 rotatably connected to the base 33. The reel assembly 35 is rotatable about an axis of rotation 37 and defines a winding surface for receiving at least a portion of the cable 29.

A first end of the cable is attached to the reel assembly 35 at a first connection point 39. From the connection point 39, the cable 29 extends through an opening 41 defined in the base 33 that maintains the direction of the cable 29 toward the lateral side 15C of the footplate 15. The cable 29 then passes through a first or posterior guide 43 located on the lateral side 15C of the footplate 15 which in turn directs the cable 29 back toward the dial-tensioning control mechanism 31. From the posterior guide 43, the cable 29 passes through a second or upper guide 45 defined in the base 33 and extends toward and passes through a third or anterior guide 47 located on the lateral side 15C of the footplate 15 which in turn directs the cable 29 toward the dial-tensioning control mechanism 31. At the dial tensioning control mechanism 31, the cable 29 enters the base 33 through an opening 51 where a second end of the cable 29 is attached to the reel assembly 35 at a second connection point 49. The opening 41 and the opening 51 can be the same or different openings.

As seen, the posterior guide 43 can be located at or near the heel of the wearer and the anterior guide 47 can be located at or near the ball of the foot or the fifth metatarsal head. The upper guide 45 can be situated at a position between the posterior guide 43 and the anterior guide 47. The reel assembly 35 can be rotated in a first direction such that a portion of the cable 29 is wound about the reel assembly 35, shortening the length of the cable 29 extending between the dial-tensioning control mechanism 31 and the footplate 15. The reel assembly 35 can also be rotated in a second direction opposite the first such that a portion of the cable 29 is unwound from the reel assembly 35, lengthening the length of the cable 29 extending between the dial-tensioning control mechanism 31 and the footplate 15.

When the ankle brace 11 is worn and the foot undergoes inversion, the lateral side 15C of the footplate 15 can tend to move with the foot away from the dial-tensioning control mechanism 31 on the lateral side 19B of the cuff 19, increasing the distance D. If present, slack in the cable 29 extending between the dial-tensioning control mechanism 31 and the footplate 15 can allow for some movement of the lateral side 15C of the footplate 15 away from the dial-tensioning control mechanism 31 on the cuff 19 but such movement is limited as the cable 29 becomes taut or reaches a hard-stop, thereby restricting and/or controlling inversion of the foot.

Because multiple lengths of the cable 29 extend through the guides and between the footplate 15 and the dial-tensioning control mechanism 31 at multiple locations, the ability of the control mechanism to limit undesired foot motion is increased.

Movement of the lateral side 15C of the footplate 15 away from the dial-tensioning control mechanism 31 on the lateral side 19B of the cuff 19 can be further limited by varying or shortening the length of the cable 29 extending between the dial-tensioning control mechanism 33 and the footplate 15. This allows a wearer to quickly and easily control the amount of tension in the cable 29 and inversion permitted by the ankle brace 11, giving the wearer the ability to customize the ankle support 11.

The motion control system 13 also allows the ankle brace 11 to be adjusted to the physical needs of the wearer. For instance, the dial-tensioning control mechanism 31 can be manipulated by the wearer to shorten or adjust the length of the cable 29 so that the wearer can participate in athletic activities or merely walk or recuperate from an ankle sprain in comfort and confidence that a new or further ankle injury will not occur. It will be further appreciated that the ankle brace 11 can be custom fitted to the wearer or for either foot.

Referring to FIG. 5, the guides 43, 45, and 47 are arranged so that the cable 29 can pass, slip and/or slide through the guides 43, 45, and 47 as the length of the cable 29 is adjusted. The cable 29 can also pass, slip, and/or slide through the guides 43, 45, and 47 as the dial-tensioning control mechanism 31 with the cuff 19 move toward and away from the anterior end 15A of the footplate 15. For instance, when the dial-tensioning control mechanism 31 moves in the direction of arrow A, a portion of the cable 29 extending between the opening 51 and the anterior guide 47 can pass through the anterior guide 47, another portion of the cable 29 extending between the anterior guide 47 and the upper guide 45 can pass through the upper guide 45, and another portion of the cable 29 extending between the upper guide 45 and the posterior guide 43 can pass through the posterior guide 43. This effectively decreases the distance between the dial-tensioning control mechanism 31 and the anterior guide 47 and increases the distance between the dial-tensioning control mechanism 31 and the posterior guide 43.

When the dial-tensioning control mechanism 31 moves in the direction of arrow B, a portion of the cable 29 extending between the opening 41 and the posterior guide 43 can pass through the posterior guide 43, another portion of the cable 29 extending between the posterior guide 43 and the upper guide 45 can pass through the upper guide 45, and another portion of the cable 29 extending between the upper guide 45 and the anterior guide 47 can pass through the anterior guide 47. This effectively decreases the distance between the dial-tensioning control mechanism 31 and the posterior guide 43 and increases the distance between the dial-tensioning control mechanism 31 and the anterior guide 47.

The cable 29 can thus pass, slip and/or slide through the guides as the dial-tensioning control mechanism 31 and/or the proximal portion 17A of the medial support 17 move with the ankle relative the anterior end 15A of the footplate 15, accommodating dorsiflexion and/or the plantar flexion of the foot. This advantageously allows the ankle brace 11 to restrict or control inversion of the foot while accommodating dorsiflexion and/or the plantar flexion of the foot, making the ankle brace 11 more comfortable and providing a more natural fit than known ankle braces.

FIG. 6 illustrates another embodiment of the orthopedic device comprising an ankle brace 61 and a motion control system 63. The ankle brace 61 can be similar to the ankle brace 11, including a footplate 65 defining an anterior end 65A and a first or medial side 65B, a second or lateral side 65C, an upright or medial support 67 defining a proximal portion 67A and a distal portion 67B, and a strap member or cuff 69.

The distal portion 67B of the medial support 67 is connected to the medial side 65B of the footplate 65 such that the proximal portion 67A of the medial support 67 can move relative to the anterior end 65A of the footplate 65.

The motion control system 63 includes a first ring assembly 71, an upper anchor element 73, a third ring assembly 75, and a tensioning element 77 configured as an elastic strap 77.

The first ring assembly 71 can be secured to the posterior area of the lateral side 65C of the footplate 65, the upper anchor element 73 can be centrally secured to the outer surface of a second or lateral side 69B of the cuff 69, and the third ring assembly 75 can be secured to the anterior area of the lateral side 65C of the footplate 65. Optionally, at least one of the upper anchor element 73 and ring assemblies 71, 75 can be pivotally secured to the footplate 65 or cuff 69. The upper anchor element 73 is shown as a second ring assembly 73 but can be any suitable anchoring element.

One end portion of the elastic strap 77 can be looped through a slot defined by the first ring assembly 71 and attached to itself via any suitable fastener including, but not limited to, stitching. From the first ring assembly 71, the elastic strap 77 extends toward the second ring assembly 73 on the cuff 69, where it passes through a slot defined by the second ring assembly 73. From there, the elastic strap 77 extends toward the third ring assembly 75 secured to the anterior area of the footplate 65. At the third ring assembly 75, a second end portion of the elastic strap 77 can be looped through a slot defined by the third ring assembly 75 and removably attached to itself via any suitable fastener including, but not limited to, a hook-and-loop type system.

The second end portion of the elastic strap 77 can be pulled further through the slot in the third ring assembly 75 and attached to itself to decrease the length of the elastic strap 77. To increase the length of the elastic strap 77, the second end portion of the elastic strap 77 can be pulled back toward the slot in the third ring assembly 75 and attached to itself.

The second ring assembly 73 is spaced apart from the lateral side 65C of the footplate 65 by a distance D1. As the motion control system 63 is manipulated to decrease the length of the elastic strap 77 and thereby increase the tension in the elastic strap 77, the lateral side 65C of the footplate 65 and the second ring assembly 73 can be urged or moved toward one another to decrease the distance D1. As the motion control system 63 is manipulated to increase the length of the elastic strap 77 and thereby decrease the tension in the elastic strap 77, slack and/or elasticity in the elastic strap 77 can permit the lateral side of the footplate 65 and the second ring assembly 73 to move apart and increase the distance D1 before the elastic strap 77 becomes taut.

When the ankle brace 61 is worn and the foot undergoes inversion, the lateral side 65C of the footplate 65 can tend to move with the foot away from the second ring assembly 73 on the lateral side 69B of the cuff 69, increasing the distance D1 between the footplate 65 and the second ring assembly 73. Slack and/or elasticity in the elastic strap 77 can allow for some movement of the lateral side of the footplate 65 away from the second ring assembly 73 on the cuff 69 but such movement is limited as the elastic strap 77 becomes taut or reaches its elastic limit, thereby restricting and/or controlling inversion of the foot. This allows for reduced or limited range of motion before the elastic strap 77 reaches a hard-stop, which may be preferable to some users.

Movement of the lateral side 65C of the footplate 65 away from the second ring assembly 73 on the cuff 69 can be further limited by shortening the length of the elastic strap 77. This allows the wearer to quickly and easily control the amount of inversion permitted by the ankle brace 61.

The second and third ring assemblies 73, 75 are arranged so that the elastic strap 77 can pass, slip and/or slide through the second and third ring assemblies 73, 75 as the length of the elastic strap 77 is adjusted. The second ring assembly 73 can also be adjusted so that the elastic strap 77 can pass, slip, and/or slide through the second ring assembly 73 as it moves with the proximal portion 67A of the medial support 67 relative to the anterior end 65A of the footplate 65, accommodating dorsiflexion and/or plantar flexion of the foot. Further, the elasticity of the elastic strap 77 can allow the second ring assembly 73 to move relative to the anterior end 65A of the footplate 65 as the elastic strap 77 stretches with the movement, helping to accommodate dorsiflexion and/or plantar flexion of the foot.

FIG. 7 illustrates another embodiment of the orthopedic device comprising a motion control system 81 having a linking system 100 arranged to dynamically link sagittal plane motion to coronal plane motion of the foot and/or vice versa. This is advantageous because a common mechanism of injury in ankle sprains is a combination of plantar flexion and inversion. By linking plantar flexion and inversion/eversion movement of the user's foot, the brace and motion control system can selectively control such movements and/or provide additional stability, facilitating range-of-motion rehabilitation, progressive muscle-strengthening exercises, proprioceptive training, and/or activity-specific training. It can also be used prophylactically for higher-risk patients or during high-risk activities such as volleyball or basketball. It should be appreciated that the motion control system 81 can be integrated with any of the ankle braces or other orthopedic devices disclosed herein.

The motion control system 81 can include an upper anchor element 83 comprising a dial-tensioning control mechanism 83 having a base 85 and a reel assembly 87 rotatably connected to the base 85. The reel assembly 87 is rotatable about an axis of rotation 89 and defines a winding surface for receiving at least a portion of the cable 91.

A first end of the cable is attached to the reel assembly 87 at a first connection point 93. From the first connection point 93, the cable 91 extends through an opening 95 defined in the base 85 that maintains the direction of the cable 91 toward the footplate. The cable 91 then passes through a posterior guide 97 located on a lateral side of the footplate which in turn directs the cable 91 back toward the dial-tensioning control mechanism 83.

From the posterior guide 97, the cable 91 passes through an upper guide 99 defined in the base 85 and is routed over a cam surface 107. From there it extends toward and passes through an anterior guide 101 located on the lateral side of the footplate which in turn directs the cable 91 toward the dial-tensioning control mechanism 83. At the tensioning control mechanism 83, the cable 91 enters the base 85 through an opening 103 where a second end of the cable 91 is attached to the reel assembly 87 at a second connection point 105.

The linking system 100 includes a cam surface 107 defined by the base 85 and a follower 109 attached along a length of the cable 91 generally corresponding to the location of the cam surface 107. The follower 109 can be a sliding or rolling member in contact with the cam surface 107 that transmits the movement dictated by the cam surface 107 to the footplate. The size and/or profile of the cam surface 107 and/or follower 109 may vary depending on the treatment protocol, application, indication, physical needs and/or characteristics of the user, and/or any other suitable factors. The location of the follower 109 along the cable 91 can be adjustable.

When the dial-tensioning control mechanism 83 moves in the direction of arrow A (e.g., during dorsiflexion of the foot), the follower 109 can slide from a neutral position (shown in FIG. 7) along the cam surface 107 in the direction of arrow B. As the follower 109 slides along the cam surface 107 in the direction of arrow B, the cam surface 107 forces the follower 109 and the cable 91 in an upward direction, which, in turn, lifts the lateral side of the footplate.

This upward movement of the lateral side footplate results in eversion of the user's foot. In other words, the cam surface 107 is effectively shortening the length of cable 91 extending between the footplate and the tensioning control mechanism 83 and thereby pulling up (proximally) on the lateral side of the footplate, resulting in eversion of the foot. Thus, the motion control system 81 dynamically links dorsiflexion of the user's foot to eversion of the user's foot, providing controlled movement of the foot in more than one plane of motion.

It will be appreciated that in other embodiments, the motion control system 81 can dynamically link plantar flexion to eversion of the user's foot. In yet other embodiments, the motion control system 81 can be arranged to dynamically link plantar flexion and/or dorsiflexion to inversion of the user's foot. While the linking system is described including a cam surface and follower, in other embodiments, the linking system can be a plate cam system, a cylindrical cam system, a face cam system, a heart shaped cam system, a linear cam system, a system including an asymmetric pivoting member, or any other suitable type of system that can link sagittal plane motion of the foot to coronal plane motion of the foot.

Figure 9:
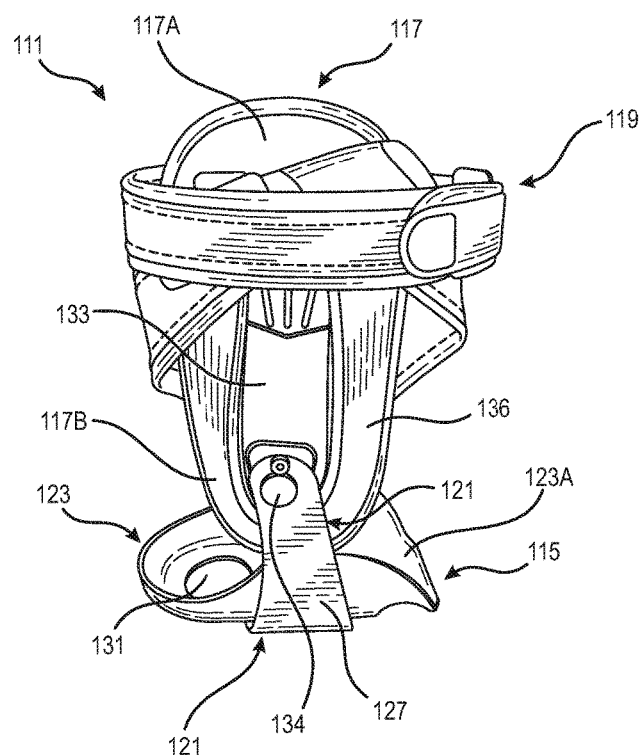
FIG. 9 is another side isometric view of the ankle brace shown in FIG. 8.
Figure 10:
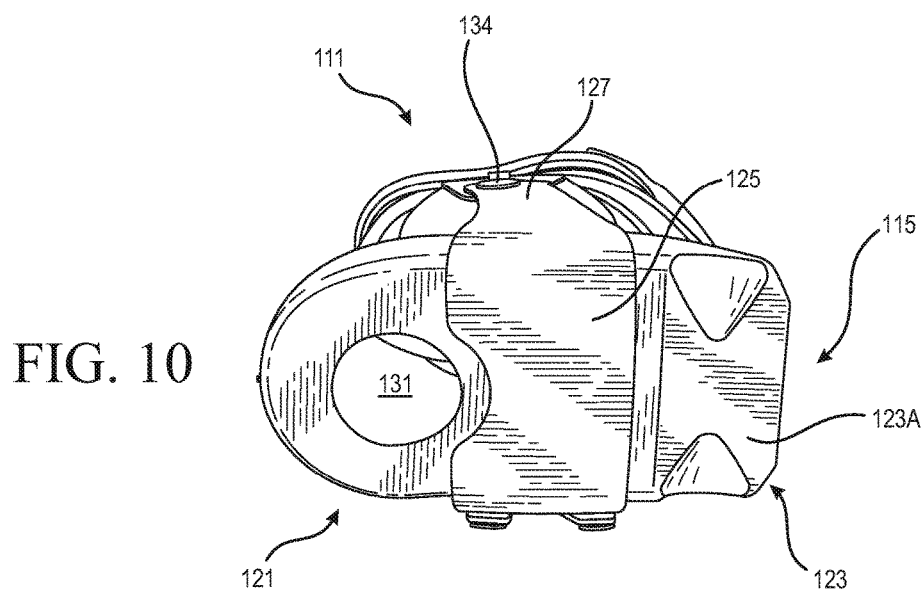
FIG. 10 is a bottom view of the ankle brace shown in FIG. 8.

FIGS. 8-10 show another embodiment of the orthopedic device comprising an ankle brace 111 and an integrated motion control system 113. Similar to the other embodiments, the ankle brace 111 controls coronal plane motion of the foot (e.g. limiting inversion/eversion), while allowing plantar flexion and dorsiflexion of the foot in the sagittal plane. The ankle brace 111 also beneficially permits custom management of the overall brace tightness or control based on a wearer's preference and/or activity level. As seen in FIG. 8, the ankle brace 111 can include a foot support or footplate 115, an upright or medial support 117, and a cuff 119.

Referring briefly to FIGS. 9 and 10, the footplate 115 includes a base portion 121 and a foot receiving portion 123 supported by the base portion 121. The foot receiving portion 123 defines an anterior end 123A and an upper surface contoured to generally correspond to the heel and middle portion of the foot and can include one or more side edges that extend around and up the heel and medial and lateral sides of the ankle. The foot receiving portion 123 can have a flexible configuration, increasing user comfort when the ankle brace 111 is worn.

Optionally, the foot receiving portion 123 can define an opening 131 arranged to receive the user's heel as shown in FIG. 10. This can increase the contact area between the user's foot and an insole or other support surface, which, in turn, helps reduce relative movement between the ankle brace 111 and footwear or orthopedic device. The foot receiving portion 123 can be formed of an elastomeric material, a plastic material, a carbon fiber composite, combinations thereof, or any other suitable material.

The base portion 121 can have a semi-rigid configuration and can include a bottom member 125 extending in a general horizontal direction under the foot receiving portion 123, between the lateral and medial sides of the foot. A first or medial member 127 can extend upwardly from the bottom member 125 on the medial side of the foot, and a second or lateral member 129 (shown in FIG. 8) can extend upwardly from the bottom member 125 on the lateral side of the foot. The medial member 127 can have a greater height than the lateral member 129. The base portion 121 can be formed of plastic, carbon fiber composite, or any other suitable material.

The medial support 117 defines a distal portion 117B connected to the footplate 115 and a proximal portion 117A arranged to move toward and away from the anterior end 123A of the footplate 115. The medial support 117 includes a shell member 133 extending along the medial side of the ankle. The shell member 133 can have a semi-rigid configuration. A soft good member 136 is provided on an inner surface of the shell member 133 and arranged to engage the medial side of the ankle, proving comfort and a proper fit of the ankle brace 111. The soft good member 136 can define a sleeve such that the shell member 133 can be received and retained within the soft good member 136. The soft good member 136 can be made from any suitable material. The shell member 133 may be formed of a carbon fiber composite, a plastic material, combinations thereof, or any other suitable material.

The cuff 119 is attached to and extends from the proximal portion 117A of the medial support 117. The cuff 119 can have a flexible or semi-flexible configuration. The cuff 119 is arranged to extend around the calf, near or just proximal of the malleoli. The cuff 119 allows the brace 111 to be easily donned and doffed and can be selectively secured around the calf so that in use the brace 111 does not undesirably slide up and down on the ankle. The cuff 119 can be attached to the medial support 117 in any suitable manner.

As best seen in FIG. 9, the distal portion 117B of the medial support 117 can be pivotally connected to the base portion 121 of the footplate 115 at a pivot axis or pivot point 134 such that the proximal portion 117A of the medial support 117 can pivot toward and away from the anterior end 123A of the footplate 115, helping to accommodate plantar flexion and dorsiflexion of the foot. The shell member 133 can be pivotally connected to the medial member 127 of the base portion 121 at the pivot point 134. Optionally, the pivot point 134 can be generally in line with the pivot of the ankle joint.

At least one strap member 135 is attached to and extends from the medial support 117. The strap member 135 can be attached to the medial support 117 in any suitable manner, such as but not limited to a hook and loop type closure. The strap member 135 can be removably attached to the medial support 117. The strap member 135 can be substantially inelastic.

The strap member 135 can extend downwardly and away from the medial support 117 such that the strap member 135 is vertically located between the footplate 115 and the cuff 119 on the lateral side of user's lower leg or ankle.

According to a variation, the strap member 135 can include two straps wrapping around the lower leg, each including a first end removably attached to the outer surface of the proximal portion 117A of the medial support 117 and a second end connected to the other strap at the lateral side of the lower leg. For instance, the second end of one of the straps can be overlapped and stitched to the second end of the other strap on the lateral side of the user's lower leg or ankle to form a V-like shape with the strap member 135.

Optionally, a pad member 137 (shown in FIG. 8) is arranged on an inner surface of the attachment strap 135 in the area of the user's malleoli on the lateral side of the foot. This can help provide cushioning and distribute pressure from the ankle brace 111 over a greater area, increasing user comfort.

Referring again to FIG. 8, the motion control system 113 can be similar to the motion control system embodiments previously described. For instance, the motion control system 113 can include a tensioning element 139 comprising a cable that is secured to an upper anchor element 141 comprising a tensioning control mechanism 141 arranged to adjust the length of the cable 139. The tensioning control mechanism 141 is not limited to but can be a dial-tensioning control mechanism.

The dial-tensioning control mechanism 141 can be secured to the outer surface of a lateral side 135B of the strap member 135, with the cable 139 extending from both the anterior and posterior sides of the tensioning control mechanism 141 to the footplate 115. It should be noted that the ends of the cable 139 are retained within the dial-tensioning control mechanism 141 and the portion of the cable 139 outside the dial-tensioning control mechanism 141 extends continuously between the footplate 115 and the dial-tensioning control mechanism without interruption. The dial-tensioning control mechanism 141 can be pivotally connected to the strap member 135 via a fastener (e.g. a rivet).

The dial-tensioning control mechanism 141 is secured to the strap member 135 below the cuff 119. This has the effect of reducing the distance between the dial-tensioning control mechanism 141 and the footplate 115. This beneficially reduces the length of cable 119 needed to extend between the dial-tensioning control mechanism 141 and the footplate, which, in turn, can reduce the weight and size of dial-tensioning control mechanism 141 because it is sized to house a smaller amount of cable 119.

The shorter run of the cable 119 between the dial-tensioning control mechanism 141 and the footplate 114 also effectively increases the stiffness of the lateral aspect of the brace. It also reduces the likelihood of pressure points or lines from the cable on user's lower leg, especially if it prevents the cable from crossing the ankle.

The cable 139 extends from the dial-tensioning control mechanism 141 toward the footplate 115 and through a posterior guide 143 located on the lateral member 129 of the foot plate 115, which, in turn, directs the cable 139 back toward the dial-tensioning control mechanism 141. From the posterior guide 143, the cable 139 passes through an upper guide 144 defined in the dial-tensioning control mechanism 141 and extends toward and passes through an anterior guide 145 located on the lateral member 129 of the footplate 115. The anterior guide 145 directs the cable 139 back toward the dial-tensioning control mechanism 141 where it is attached to reel assembly.

The posterior and anterior guides 143, 145 are located within a longitudinal arch area of the footplate 115 almost directly below the dial-tensioning control mechanism 141. Such a spatial relationship between the dial-tensioning control mechanism 141 and the guides 143, 145 increases the vertical component and decreases the horizontal component of the force exerted on the footplate 115 by the cable 139. This can help increase the upward influence of the cable 139 on the footplate 115 as compared to where the posterior and anterior guides are separated by a greater horizontal distance.

The dial-tensioning control mechanism 141 can be rotated in a first direction such that a portion of the cable 139 is wound about its reel assembly, shortening the length of the cable 139 extending between the dial-tensioning control mechanism 141 and the footplate 115. This in turn can pull the connection formed between the dial-tensioning control mechanism 141 and the strap member 135 toward the footplate, which, in turn, is counteracted by the medial support 117, causing the strap member 135 to apply a load on the posterior aspect (e.g., Achilles tendon) or on the anterior aspect (e.g., tibia) of the wearer's lower leg or ankle as the circumference it forms decreases. It will be appreciated that such applied loads can be used in treatment of the ankle, foot, lower leg, or knee.

The dial-tensioning control mechanism 141 can also be rotated in a second direction opposite the first such that a portion of the cable 139 is unwound from the reel assembly, lengthening the length of the cable 139 extending between the dial-tensioning control mechanism 141 and the footplate 115.

The dial-tensioning control mechanism 141 is spaced apart from the lateral side of the footplate 115 by a distance D2. When the ankle brace 111 is worn and the foot undergoes inversion, the lateral side or lateral member 129 of the footplate 115 can tend to move with the foot away from dial-tensioning control mechanism 141, increasing the distance D2. If present, slack in the cable 139 extending between the dial-tensioning control mechanism 141 and the footplate 115 can allow for some movement of the lateral side of the footplate 115 away from the cuff 119 but such movement is limited as the cable 139 becomes taut or reaches a hard-stop and/or is counteracted by the medial support 117, thereby restricting and/or controlling inversion of the foot.

Movement of the lateral side or lateral member 129 of the footplate 115 away from the dial-tensioning control mechanism 141 can be further limited by shortening the length of the cable 139 extending between the dial-tensioning control mechanism 141 and the footplate 115. This allows a wearer to quickly and easily control the amount of tension in the cable 139 and inversion permitted by the ankle brace 111, giving the wearer the ability to customize the ankle brace 111.

The motion control system 113 also allows the ankle brace 111 to be adjusted to the physical needs of the wearer. For example, the dial-tensioning control mechanism 141 can be manipulated by the wearer to shorten the length of the cable 139 so that the wearer can participate in athletic activities or merely walk or recuperate from an ankle sprain in comfort and confidence that a new or further ankle injury will not occur. It will be further appreciated that the ankle brace 111 can be custom fitted to the wearer or for either foot.

Like in the previous embodiments, the guides for the cable 139 are arranged so that the cable 139 can move, pass, slip, or slide through the guides. The cable 139 can thus pass, slip and/or slide through the guides as the dial-tensioning control mechanism 141 on the strap member 135 moves with the ankle relative the anterior end 123A of the footplate 115, helping to accommodate dorsiflexion and/or the plantar flexion of the foot. This advantageously allows the ankle brace 111 to control inversion of the foot while accommodating dorsiflexion and/or the plantar flexion of the foot, making the ankle brace more comfortable and providing a more natural fit than known ankle braces.

The cable 139 can also move through the guides as the length of the cable 139 is adjusted using the dial-tensioning control mechanism.

It will be appreciated that the embodiments described herein are to be regarded as exemplary only, as any orthopedic device is possible. For instance, in other embodiments, the upper anchor element can be located on the outer surface of the medial support and the cable can be routed through the strap member to the upper anchor element. The arrangement of the cable extending through the strap member can be adapted to vary the load exerted on the lower leg by the strap member.

In yet other embodiments, the support member of the medial support can be integrated or included with the foot receiving portion of the footplate 115. The motion control system is also not limited to a single cable or a single upper anchor element, but it is possible that multiple cables and upper anchor elements may be used to urge or move the lateral side of the cuff relative to the footplate.

In other embodiments, the tensioning element can pass through more connection points between the upper anchor element and the footplate, decreasing the force required to urge or move the lateral side of the cuff toward the footplate. In yet other embodiments, the medial support can comprise a lateral support arranged to be positioned on the lateral side of the ankle and the motion control system can be located on the medial side of the cuff such that the motion control system can restrict or control eversion of the foot.

In yet other embodiments, the motion control system and medial support can be arranged to be positioned on the same side of the ankle. In yet other embodiments, the tensioning element can be a non-elastic strap, a rope, a braided strap, any other suitable tensioning element. In yet other embodiments, the footplate can include a single guide having an elongated configuration extending along the second or lateral side of the footplate. As such, the tensioning element can form a triangular shape or path between the tensioning control mechanism and the single guide.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. An orthopedic device comprising:
   a footplate arranged to be positioned beneath a foot of a wearer, the footplate defining an anterior end, a first side, and a second side opposite the first side, the second side including a first guide;
   an upright support having a semi-rigid configuration and arranged to extend along a side of an ankle of the wearer, the upright support including a distal portion connected to the first side of the footplate and a proximal portion arranged to move toward and away from the anterior end of the footplate;
   a cuff having a flexible configuration including a first portion affixed to the proximal portion of the upright support, and a second portion extending over the second side of the footplate and arranged to move toward and away from the second side of the footplate; and
   a motion control system including a dial-tensioning control mechanism attached to the second portion of the cuff above the second side of the footplate, and at least one tensioning element including first and second ends affixed to the dial-tensioning control mechanism and passing through the first guide of the footplate toward a second guide defined on the dial-tensioning control mechanism that directs the at least one tensioning element back towards the footplate,
   wherein the at least one tensioning element is arranged to allow movement of the second side footplate in a direction away from the cuff until the at least one tensioning element becomes taut and to slide through the first guide on the footplate and to slide through the second guide on the dial-tensioning control mechanism when the proximal portion of the upright support moves toward and away from the anterior end of the footplate.

2. The orthopedic device of claim 1, further comprising a strap member arranged to extend around a calf below the cuff, the strap member including first and second end portions removably attached to the upright support above the first side of the footplate.

3. The orthopedic device of claim 1, wherein the at least one tensioning element is arranged to pass and slide through a third guide longitudinally spaced from the first guide on the second side of the footplate.

4. The orthopedic device of claim 3, wherein the second guide directs the at least one tensioning element toward the first and third guides.

5. The orthopedic device of claim 1, wherein the distal portion of the upright support is pivotally connected to the first side of the footplate such that the proximal portion of the support pivotally moves toward and away from the anterior end of the footplate.

6. The orthopedic device of claim 1, wherein the dial-tensioning control mechanism includes a base and the second guide is defined in the base.

7. The orthopedic device of claim 1, wherein when the at least one tensioning element slides through the second guide the at least one tensioning element lifts the second side of the footplate relative to the first side of the footplate.

8. The orthopedic device of claim 1, wherein the first side is a medial side of the footplate and the second side is a lateral side of the footplate.

9. The orthopedic device of claim 1, wherein the dial-tensioning control mechanism is arranged for incremental and preselected adjustment in the tension of the at least one tensioning element.

10. The orthopedic device of claim 9, wherein the dial-tensioning control mechanism is rotatable in a first direction to decrease a length of the at least one tensioning element outside of the dial-tensioning control mechanism.

11. The orthopedic device of claim 9, wherein slack in the at least one tensioning element extending between the dial-tensioning control mechanism and the second side of the footplate allows for the movement of the second side of the footplate away from the dial-tensioning control mechanism until the at least one tensioning element becomes taut.

12. An orthopedic device comprising:
a footplate arranged to be positioned beneath a foot of a wearer, the footplate defining an anterior end, a first side, and a second side opposite the first side and including a first guide;
an upright support having a semi-rigid configuration and arranged to extend along a side of an ankle of the wearer, the upright support including a proximal portion and a distal portion, the distal portion pivotally connected to the first side of the footplate such that the proximal portion of the upright support pivotally moves toward and away from the anterior end of the footplate;
a cuff having a flexible configuration affixed to the proximal portion of the upright support, the cuff arranged to extend around a calf of the wearer; and
a motion control system including a dial-tensioning control mechanism attached to the cuff above the second side of the footplate, and at least one tensioning element including first and second ends affixed to the dial-tensioning control mechanism and passing through the first guide of the footplate toward a second guide defined on the dial-tensioning control mechanism that directs the at least one tensioning element back towards the footplate,
wherein the at least one tensioning element slides through the first guide on the footplate and through the second guide on the dial-tensioning control mechanism and lifts the second side of the footplate above the first side of the footplate when the proximal portion of the upright support pivotally moves away from the anterior end of the footplate.

13. An orthopedic device comprising:
a footplate arranged to be positioned beneath a foot of a wearer, the footplate defining an anterior end, a first side, and a second side opposite the first side and including a first guide;
an upright support having a semi-rigid configuration and arranged to extend along a side of an ankle of the wearer, the upright support including a proximal portion and a distal portion, the distal portion pivotally connected to the first side of the footplate such that the proximal portion of the upright support pivotally moves toward and away from the anterior end of the footplate;
a cuff having a flexible configuration affixed to the proximal portion of the upright support, the cuff arranged to extend around a calf of the wearer;
a motion control system including a dial-tensioning control mechanism attached to the cuff above the second side of the footplate, and at least one tensioning element including first and second ends affixed to the dial-tensioning control mechanism and passing through the first guide of the footplate toward a second guide defined on the dial-tensioning control mechanism that directs the at least one tensioning element back towards the footplate, wherein the at least one tensioning element is arranged to allow movement of the second side footplate in a direction away from the dial-tensioning control mechanism until the at least one tensioning element becomes taut and to slide through the first guide on the footplate and through the second guide on the dial-tensioning control mechanism when the proximal portion of the support pivotally moves toward and away from the anterior end of the footplate; and
a strap member arranged to extend around the calf of the wearer below the cuff, the strap member including first and second end portions removably attached to the support above the first side of the footplate, the dial-tensioning control mechanism attached to the strap member above the second side of the footplate.

14. The orthopedic device of claim 13, wherein the dial-tensioning control mechanism dynamically links coronal and sagittal plane motion of the foot of the user.

* * * * *